(12) United States Patent  (10) Patent No.: US 8,292,858 B2
Burgess et al.  (45) Date of Patent: Oct. 23, 2012

(54) DRAIN BAG VALVE AND SHIELD

(75) Inventors: James E. Burgess, Long Grove, IL (US); Jennifer T. Swartz, Libertyville, IL (US); Earl D. Wilson, Ingleside, IL (US); Alberto C. Savage, Buffalo Grove, IL (US); Dale F. Greeson, Jr., Palatine, IL (US); Jack E. Maze, Long Grove, IL (US)

(73) Assignee: Medline Industries, Inc., Mundelein, IL (US)

( * ) Notice: Subject to any disclaimer, the term of this patent is extended or adjusted under 35 U.S.C. 154(b) by 792 days.

(21) Appl. No.: 12/180,190

(22) Filed: Jul. 25, 2008

(65) Prior Publication Data

US 2009/0030379 A1  Jan. 29, 2009

Related U.S. Application Data

(60) Provisional application No. 60/962,043, filed on Jul. 25, 2007.

(51) Int. Cl.
*A61M 1/00* (2006.01)

(52) U.S. Cl. .......... 604/323; 604/326; 604/322

(58) Field of Classification Search .......... 604/323, 604/322, 326, 249
See application file for complete search history.

(56) References Cited

U.S. PATENT DOCUMENTS

| | | | |
|---|---|---|---|
| 3,415,299 A | 12/1968 | Hinman, Jr. et al. | |
| 3,529,599 A | 9/1970 | Folkman | |
| 3,823,716 A * | 7/1974 | Hale | 604/322 |
| 3,908,656 A | 9/1975 | Binard | |
| 4,109,837 A * | 8/1978 | Taylor | 222/556 |
| 4,154,264 A * | 5/1979 | Schaller | 138/26 |
| 4,254,771 A | 3/1981 | Vidal | |
| 4,280,498 A * | 7/1981 | Jensen | 604/335 |
| 4,333,480 A | 6/1982 | Villari et al. | |
| 4,372,313 A | 2/1983 | Villari et al. | |
| 4,465,479 A | 8/1984 | Meisch | |
| 4,537,387 A * | 8/1985 | Danby et al. | 251/331 |
| 4,540,156 A * | 9/1985 | Cross | 251/309 |
| 4,573,983 A * | 3/1986 | Annis | 604/322 |
| 4,634,437 A | 1/1987 | Lowthian | |
| 4,693,712 A * | 9/1987 | Bates | 604/323 |
| 4,725,268 A * | 2/1988 | Ostensen et al. | 604/323 |
| 4,728,324 A * | 3/1988 | Steigerwald et al. | 604/323 |
| 4,769,003 A * | 9/1988 | Stamler | 604/39 |
| D300,361 S * | 3/1989 | Tokarz | D24/129 |
| 4,815,477 A | 3/1989 | McWhorter et al. | |
| 4,909,478 A * | 3/1990 | Steer | 251/352 |
| 5,019,102 A * | 5/1991 | Hoene | 623/23.66 |

(Continued)

*Primary Examiner* — Susan Su

(74) *Attorney, Agent, or Firm* — Nixon Peabody LLP

(57) ABSTRACT

A drain bag outlet device includes inlet, valve and outlet portions. The inlet portion includes a connector and a cylindrical portion. The connector is adapted to connect to a fluid drain bag. A second end of the connector is adapted to connect to the cylindrical portion forming a generally longitudinal opening therethrough. The valve portion is attached to a second end of the cylindrical portion and includes a valve member for moving between positions to permit and obstruct fluid flow through the longitudinal opening. The outlet portion includes an outlet member having an angled portion and a shield connected to the valve portion. The shield completely surrounds and extends below the outlet member. The shield includes upper and lower portions. The diameter of the upper is less than the diameter of the lower portion. The outlet device eliminates the fluid that is spilled, splashed or sprayed on a healthcare worker.

32 Claims, 6 Drawing Sheets

U.S. PATENT DOCUMENTS

| | | | | |
|---|---|---|---|---|
| 5,084,035 | A | 1/1992 | Salvadori et al. | |
| 5,384,918 | A * | 1/1995 | Leighton et al. | 4/255.05 |
| 5,441,174 | A * | 8/1995 | Sperry | 222/105 |
| 5,833,654 | A * | 11/1998 | Powers et al. | 604/93.01 |
| 6,132,407 | A | 10/2000 | Genese et al. | |
| 6,156,004 | A * | 12/2000 | Tremaine et al. | 604/27 |
| 6,261,254 | B1 | 7/2001 | Baron et al. | |
| 6,482,190 | B1 | 11/2002 | Genese et al. | |
| 6,553,779 | B1 * | 4/2003 | Boyer et al. | 62/342 |
| 6,626,884 | B1 * | 9/2003 | Dillon et al. | 604/409 |
| 7,175,612 | B2 * | 2/2007 | Felix et al. | 604/323 |
| 2004/0116903 | A1 * | 6/2004 | Osman | 604/543 |
| 2004/0215155 | A1 | 10/2004 | Wolfe et al. | |
| 2005/0124946 | A1 | 6/2005 | Landau et al. | |
| 2005/0148958 | A1 | 7/2005 | Rucinski | |
| 2006/0025724 | A1 * | 2/2006 | Chen | 604/249 |
| 2008/0108955 | A1 * | 5/2008 | Blickhan | 604/248 |
| 2008/0298164 | A1 * | 12/2008 | Wilson | 366/129 |
| 2009/0204080 | A1 * | 8/2009 | Balteau et al. | 604/249 |

* cited by examiner

DRAIN BAG VALVE AND SHIELD

CROSS-REFERENCE TO RELATED APPLICATION

This application claims the benefit of U.S. Provisional Application No. 60/962,043 filed Jul. 25, 2007, which is hereby incorporated by reference in its entirety.

FIELD OF THE INVENTION

The present invention relates to drain bag valves and shields, and more particularly to drain bag valves and shields for urinary drain bags. The drain bag valve and shield of the present invention reduces the occurrence of urine being trapped on the end of the outlet and, thus, reduces the risk of spilling, splashing or spraying urine on healthcare workers.

BACKGROUND

Urinary drain bags are often used by healthcare personnel to collect urine from catheterized patients. To permit fluid to be drained from a urinary drain bag, healthcare personnel may open an outlet port at or near the bottom portion of the drain bag. Typically, the outlet port is comprised of tubing which is clamped off to prevent fluid from draining from the drain bag. A healthcare worker may unclamp the tubing to obtain a urine sample.

After taking a urine sample, the healthcare worker may place the clamped tubing into a housing, often called a drain housing or "keeper," which holds the tubing to prevent it from becoming contaminated. Alternatively, a healthcare worker may place the tubing alongside the drain bag to keep the tube close to the drain bag and away from possible sources of contamination. These practices, however, often allow urine to be spilled, splashed or sprayed onto the healthcare worker as he or she attempts to place the tubing in the housing or to mount the tubing next to the drain bag. Splashing or spraying may also occur when the healthcare worker takes the tubing out of the housing or away from the drain bag to obtain another urine sample.

Therefore, there is a need to provide healthcare workers with an outlet device for urinary drain bags having a valve and shield which reduces the occurrence of spilling, splashing or spraying of urine while at the same time protecting the device from possible contamination. Furthermore, it is desirable that any such outlet device not require additional work by the healthcare worker such as holding a drainage outlet in place while taking a urine sample. While many outlet devices require healthcare workers to use two hands when taking a urine sample to reduce the chance of spilling, splashing or spraying the urine, it is advantageous to have a device that reduces such spilling, splashing or spraying so that only one hand is necessary to obtain the urine sample. This allows healthcare workers to use their other hand to attend to other details while caring for patients.

SUMMARY

In one embodiment, an outlet device for connecting to a fluid drain bag and adapted to eliminate the use of a drain housing comprises an inlet portion, a valve portion and an outlet portion. The inlet portion includes a connector and a cylindrical portion. The first end of the connector is adapted to connect to the fluid drain bag and a second end of the connector is adapted to connect to a first end of the cylindrical portion thereby forming a generally longitudinal opening therethrough. The valve portion is connected to a second end of the cylindrical portion and further forms the longitudinal opening. The valve portion contains a valve member for moving between a first position for permitting fluid flow through the longitudinal opening and a second position for obstructing fluid flow through the longitudinal opening. The outlet portion is connected to the valve portion. The outlet portion includes a shield and an outlet member surrounded by the shield. The shield extends a distance below the outlet member and has an upper portion and a lower portion wherein the diameter of the upper portion is less than the diameter of the lower portion. The outlet member is in fluid communication with the longitudinal opening of the valve portion and the inlet portion and includes an angled end portion for reducing the amount of fluid that may collect on the perimeter of the outlet member.

According to another embodiment, a container system for collecting and discharging fluid comprises a chamber for holding fluid and an outlet device. The outlet device is connected to the chamber. The outlet device comprises an inlet portion, a valve portion and an outlet portion. The inlet portion includes a connector and a cylindrical portion. A first end of the connector is adapted to connect to the chamber and a second end of the connector is adapted to connect to a first end of the cylindrical portion thereby forming a generally longitudinal opening therethrough which is in fluid communication with the chamber. The valve portion is connected to a second end of the cylindrical portion and contains a valve member for moving between a first position for permitting fluid flow through the longitudinal opening and a second position for obstructing fluid flow through the longitudinal opening. The outlet portion is attached to the valve portion and includes a shield and an outlet member in fluid communication with the longitudinal opening. The shield completely surrounds the outlet member and extends below the outlet member. The shield has an upper portion and a lower portion wherein the diameter of the upper portion is less than the diameter of the lower portion. The outlet member has an angled end portion for directing fluid as it flows through the longitudinal opening. The outlet device is in fluid communication with the chamber such that a portion of the fluid can be removed from the chamber by moving the valve member from the first position to the second position and allowing fluid to flow through the outlet device.

The above summary is not intended to represent each embodiment or every aspect of the present invention. The detailed description and Figures will describe many of the embodiments and aspects of the present invention.

BRIEF DESCRIPTION OF THE DRAWINGS

The foregoing and other advantages of the invention will become apparent upon reading the following detailed description and upon reference to the drawings.

Figure 1:
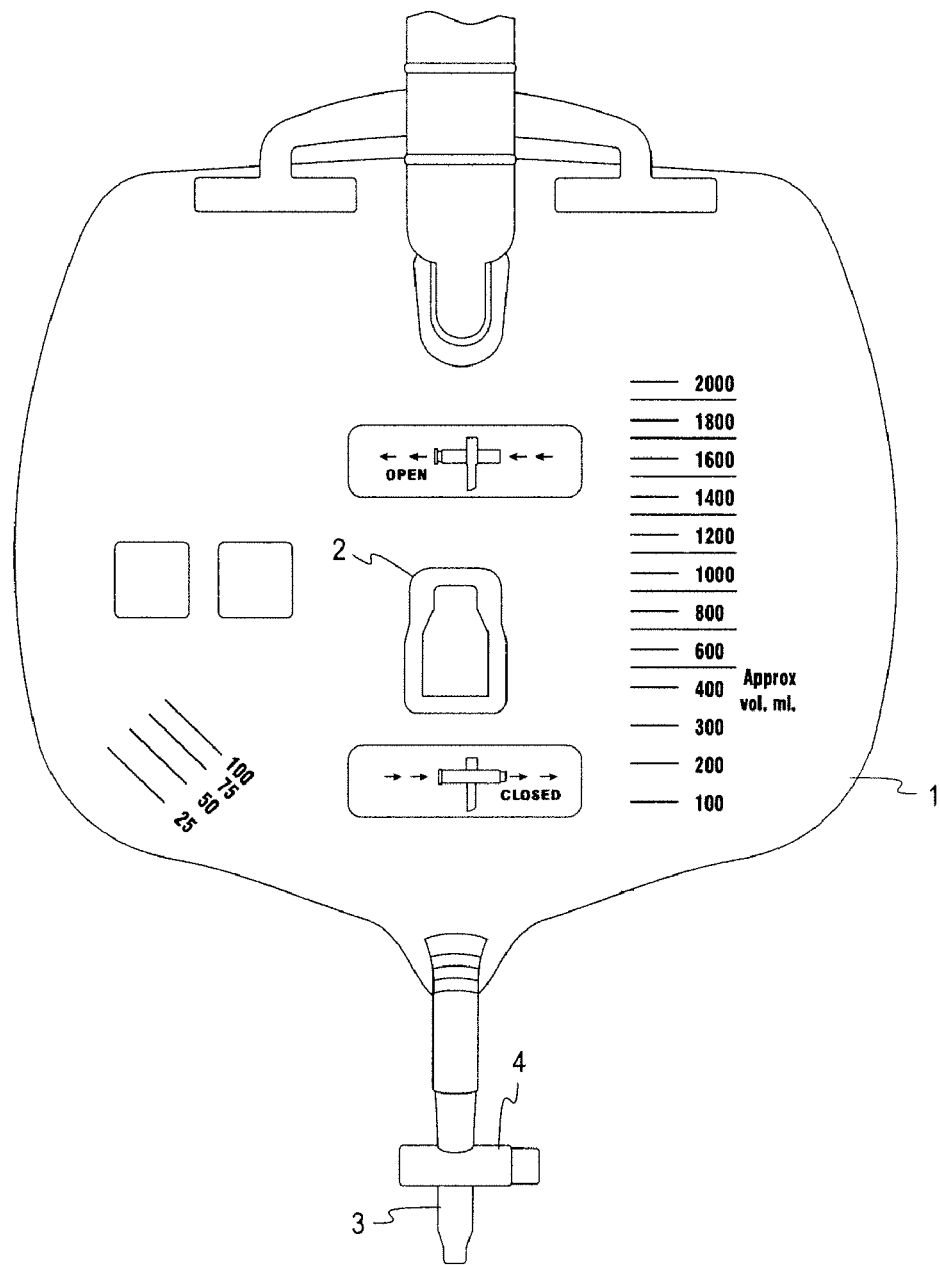
FIG. 1 is a perspective view of a prior art drain bag including a drain housing.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF THE ILLUSTRATED EMBODIMENTS

Figure 2:
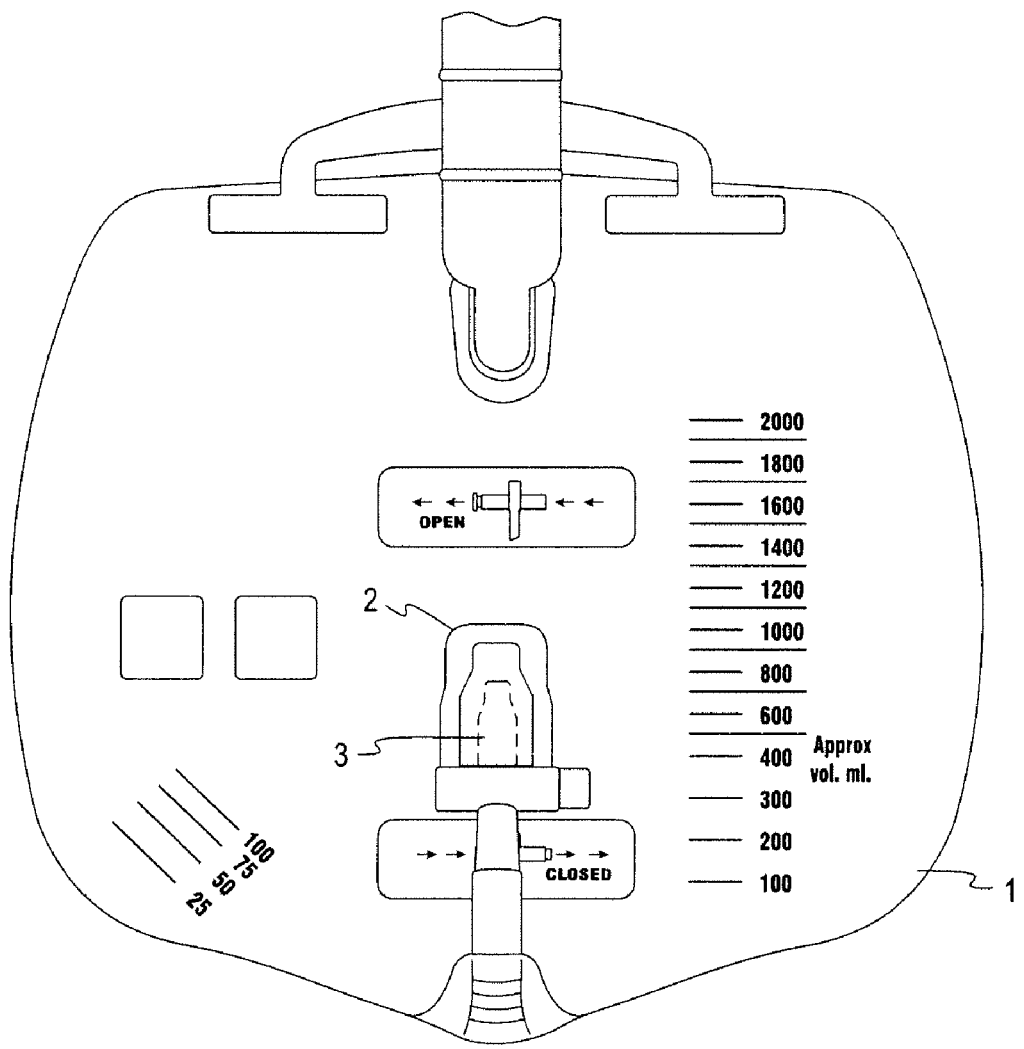
FIG. 2 is a perspective view of the prior art drain bag of FIG. 1 showing the drain housing holding a tubing near the center of the drain bag.
Figure 3:
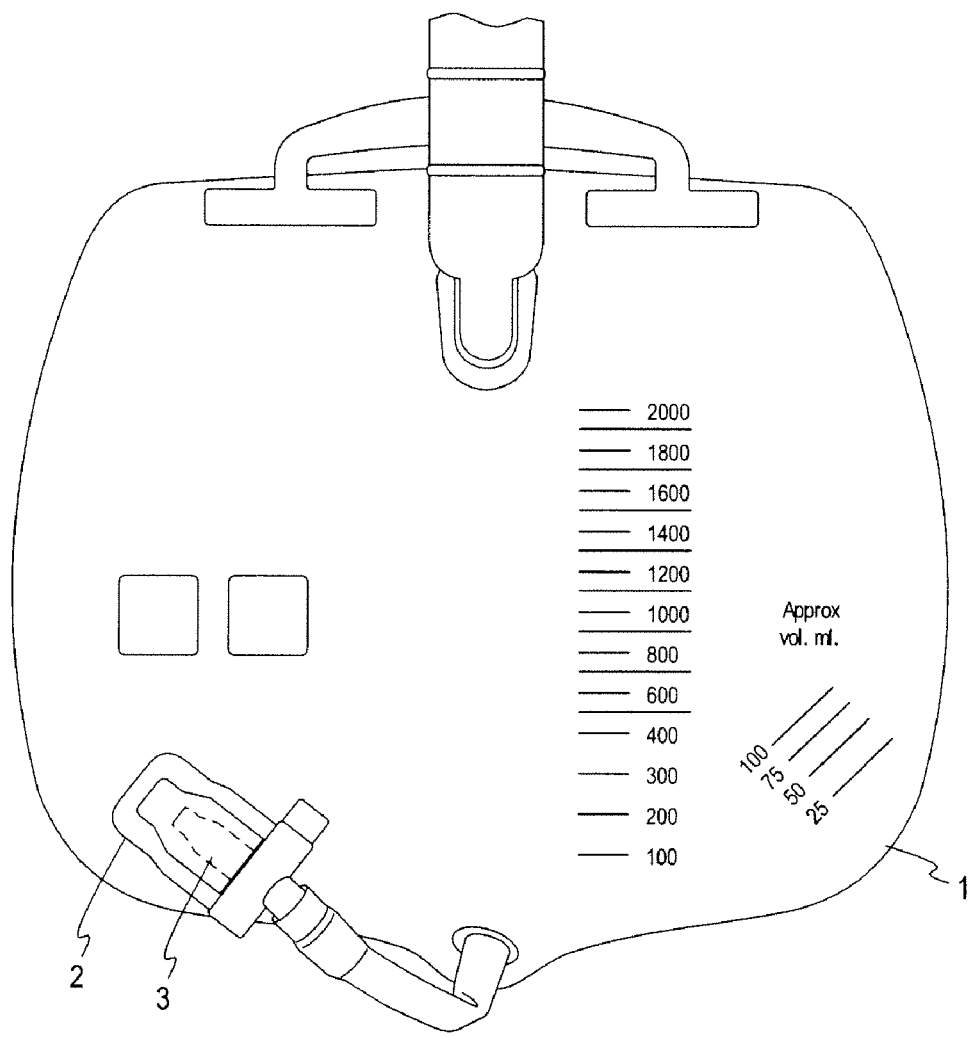
FIG. 3 is a perspective view of another prior art drain bag showing the drain housing holding a tubing at a side of the drain bag.

Referring to the drawings, FIGS. 1-3 are perspective views of drain bags of the prior art. The prior art drain bag 1 has a drain housing or keeper 2 for holding tubing 3 after a sample has been withdrawn through an outlet system 4. FIG. 1 shows the tubing 3 before it has been placed in the drain housing 2. The drain housing 2 may be attached to the drain bag 1 near the center of the drain bag 1 directly above the outlet system 4 (as shown in FIGS. 1 and 2) or may be attached on the side of the drain bag 1 (as shown in FIG. 3). The drain housing 2 holds the tubing 3 to keep the tubing 3 from contacting possible sources of contamination (as shown in FIGS. 2 and 3).

Figure 4:
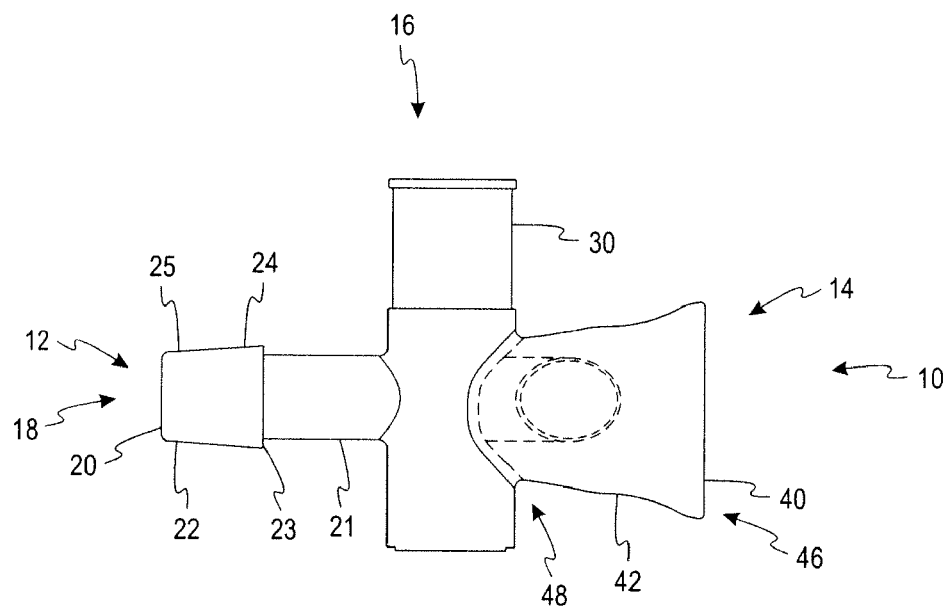
FIG. 4 is a side view of an outlet device according to one embodiment of the present concepts.

The outlet device 10 of the present concepts described herein does not require a drain housing 2 as do the prior art drain bags 1. One such embodiment shown in FIG. 4 includes a single integrated outlet device 10 for attaching to a drain bag. As described below, the integrated outlet device 10 reduces or eliminates the spilling, splashing and spraying of fluid onto a healthcare worker when a sample of fluid is being withdrawn from a drain bag. The outlet device 10 also reduces the possibility of contamination due to bacteria contacting the end of the outlet device 10 and traveling upwards to the patient through the drain bag, without requiring that the outlet device 10 be stored in a drain housing 2. In alternative embodiments, the outlet device 10 may not be an integrated device but may have separate parts that may be attached or removed by a healthcare worker.

The outlet device 10 comprises an inlet portion 12, an outlet portion 14 and a valve portion 16. The outlet device 10 also includes a generally longitudinal opening 18 therethrough allowing fluid to flow from the inlet portion 12 through the valve portion 16 to be discharged from the outlet portion 14. As described below in more detail, the outlet device 10 is attached to a drain bag and allows fluid from the drain bag (not shown) to be withdrawn through the outlet device 10 such that the spilling, spraying or splashing of the fluid on a healthcare worker is minimized or eliminated. While it is envisioned that the outlet device described herein may be particularly useful with urinary drain bags, it is also contemplated the outlet device may be used with other types of fluid drain bags.

The inlet portion 12 of the outlet device 10 includes an inlet opening 20, a generally cylindrical portion 21 and a connector 22. The shape of the inlet opening 20, cylindrical portion 21 and connector 22 may be circular, oval, square or other shapes, and may depend on the method of connecting the outlet device 10 to the drainage bag and/or the shape of the shield 42 and outlet member 44 (described below). The connector 22 includes a flange 23 for inserting into tubing at or near the bottom portion of a drain bag (not shown). The circumference of the connector 22 is greater at the distal end 24 of the connector 22 than at the proximal end 25 of the connector 22, due to the flange 23 projecting outwardly at the distal end 24 of the connector 22. This causes the connector 22 to remain in the tubing of the drain bag once the outlet device 10 is attached to the drain bag. The connector 22, once attached to the drain bag, causes the outlet device 10 to be in fluid communication with a chamber in the drain bag for holding the fluid collected from a patient. Other suitable forms of attaching the outlet device 10 to the drain bag may be used.

The distal end 24 of the connector 22 may be integrally formed with the generally cylindrical portion 21. The connector 22 may also be manufactured separately from the cylindrical portion 21 and then connected to the cylindrical portion 21 through a process such as, but not limited to, solvent bonding or a snap-on process. Other forms of attachment which are suitable to attach the cylindrical portion 21 to the connector 22 may be used. Together, the cylindrical portion 21 and the connector 22 form the longitudinal opening 18 that is in fluid communication with the chamber of the drain bag.

The cylindrical portion 21 may be integrally formed with the valve portion 16 that is also generally cylindrical in shape. The cylindrical shape may, in some cases, reduce leaking of fluid from the outlet device 10. The valve portion 16 may also be circular, oval, square or other shapes. The vertical axis of the valve portion 16 generally runs perpendicular to the flow of fluid through the outlet device 10. The valve portion 16 is adapted to receive a valve member 30. The valve member 30 is movable within the valve portion 16 in a direction generally perpendicular to the flow of fluid through the outlet device 10. To allow fluid to flow through the outlet device 10, the valve portion 16 and the valve member 30 include a hole (not shown), that is in fluid communication with the generally longitudinal opening 18.

In the embodiment depicted in FIGS. 4-7, the valve member 30 is a slide valve that is movable from a first position to a second position. In the first position or the "open" position, the valve member 30 is positioned such that the hole in the valve member 30 is in alignment with the longitudinal opening 18. This permits fluid to move from the drain bag, through the inlet portion 12 and valve portion 16 and out through the outlet portion 14. In the second position or "closed" position, the valve member 30 is positioned such that the longitudinal opening 18 is obstructed by the valve member 30 so that fluid is not able to move from the inlet portion 12 to the outlet portion 14. Although the embodiments described herein and shown in the drawings include a valve member 30 that is a slide valve, it is contemplated that other types of valve members may be used, such as clamp valves or other valves that allow fluid flow to be impeded at the will of a healthcare worker.

As described above, fluid flows from the drain bag through the inlet portion 12 and the valve portion 16 (when in the "open" position) and out through the outlet portion 14. The outlet portion 14 may be integrally formed with the valve portion 16 and the inlet portion 12. The outlet portion 14 includes an outlet opening 40, a shield 42 and an outlet member 44 that is in fluid communication with the hole of the valve portion 16. As will be described in more detail below, the combination of the outlet member 44 and the shield 42 directs the fluid as it flows through the outlet device 10 and minimizes the occurrence of fluid being spilled, sprayed or splashed onto a healthcare worker.

It is contemplated that different methods may be used to connect the inlet portion 12, the outlet portion 14 and the valve portion 16. In some embodiments, one or more of the inlet portion 12, the outlet portion 14 and the valve portion 16 may be separate components that are attachable as a single unit. For example, the outlet device 10 may be manufactured having one or more components that are removable, such as a separate shield 42 that may be snapped or adhered, such as by adhesion bonding or solvent bonding, to the valve portion 16 and may be removable at will. It is contemplated that the shield 42 and other components of the outlet device 10 may be attached using other suitable connection methods. In addition, the inlet portion 12, the outlet portion 14 and the valve portion 16 themselves may be made up of separate elements that can be connected to form each of the individual components or, alternatively, the inlet portion 12, the outlet portion 14 and the valve portion 16 may be a single integrated unit.

Figure 5:
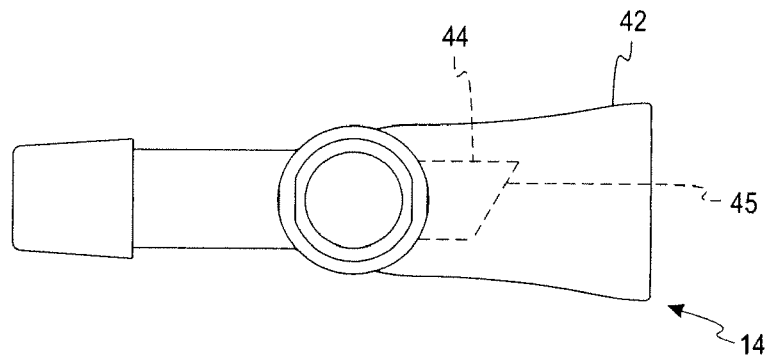
FIG. 5 is a top view of the outlet device of FIG. 4.
Figure 6:
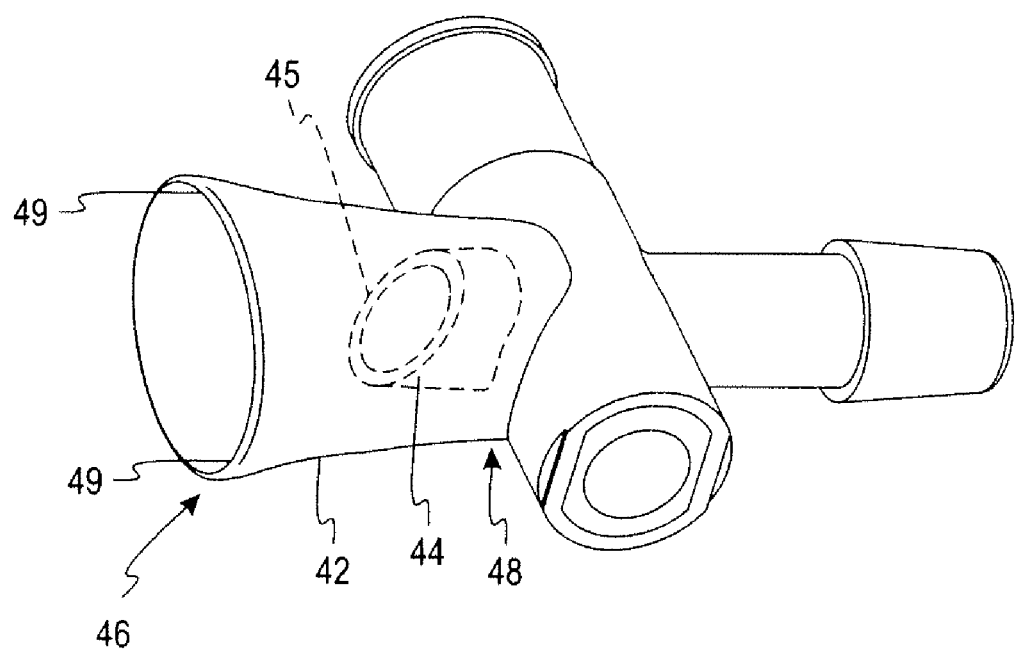
FIG. 6 is a bottom view of the outlet device of FIG. 4.

As shown in FIG. 5, the outlet member or stem 44 may include an angled end portion 45 to assist in directing fluid as it leaves the outlet device 10. Having an end portion 45 of the outlet member 44 that is angled reduces the amount of fluid that may collect on the perimeter of the outlet member 44. Such a design allows urine to drip from the angled end portion 45 of the outlet member 44 rather than collect on the perimeter of the outlet member 44. This design is also desirable as it allows larger droplets to be formed which lessens the likelihood of spraying of the fluid onto a healthcare worker. The angled end portion 45 of the outlet member 44 may range from approximately 0 to approximately 90 degrees with respect to the axis of fluid flow through the outlet device 10, and is desirably about 45 degrees. If the angled end portion 45 of the outlet member 44 is more or less than about 45 degrees, then larger drops may not form as well or may not collect on the angled end portion 45.

As discussed above, FIGS. 4-7 illustrate an outlet device 10 that reduces the tendency for fluid to collect on the perimeter of the outlet member 44 as it flows through the outlet device 10. This is desirable for healthcare workers who want to avoid having the fluid that flows through the outlet device 10 spilled, splashed or sprayed on their face, hands or body. The shape of the shield 42 also contributes to a reduction in and/or elimination of splashing and spraying of fluid onto the healthcare worker. The shield 42 shown in FIGS. 4-7 is bell-shaped such that the diameter of the lower portion 46 of the shield 42 is larger than the diameter of the upper portion 48 of the shield 42 for all axes.

Figure 7:
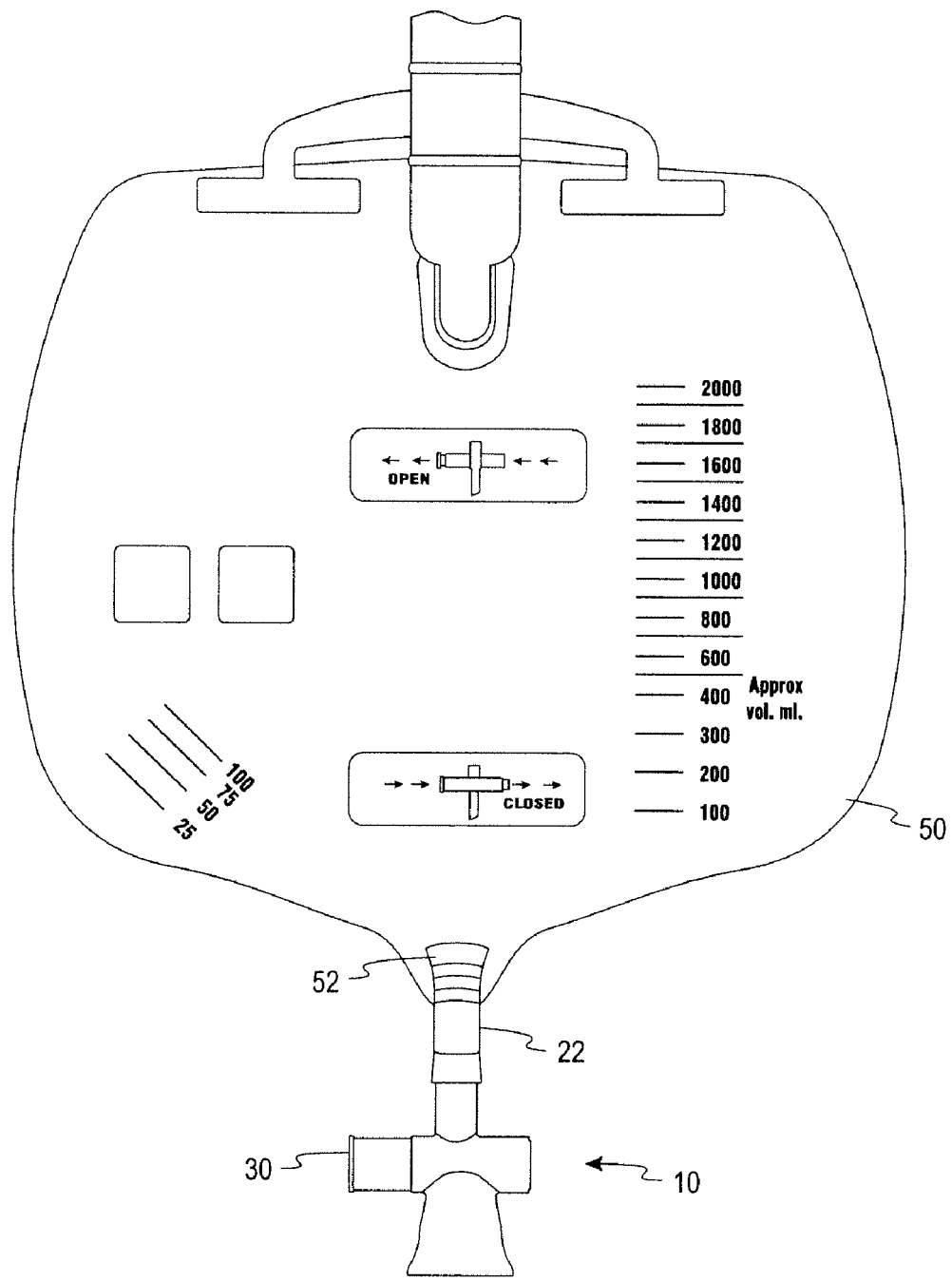
FIG. 7 is a perspective view of the outlet device of FIG. 4 attached to a drain bag.

The bell-shaped design of the shield 42 reduces or prevents the occurrence of urine being trapped on the sidewalls 49 (shown in FIG. 6) of the shield 42 when a sample of fluid is withdrawn from the drain bag (see FIG. 7). The sidewalls 49 of the shield 42 are farthest from the outlet member 44 at the lower portion 46 of the shield 42 and, therefore, are less likely to be contacted with the stream of fluid exiting the outlet member 44. Thus, spilling, splashing or spraying of fluid onto healthcare workers is reduced and/or eliminated. Furthermore, the shield 42 extends a sufficient distance below the outlet member 44 to reduce accidental contact with the outlet member 44.

The shield 42 may be oval-shaped as shown in FIGS. 4-7. The oval shape may be advantageous over circular-shaped shields as the oval-shaped shield requires smaller, thinner packaging due to the smaller diameter along at least one of the axes. Although an oval shape may be desirable for packaging purposes, it is also contemplated that other shapes, such as circular, rectangular, square, or other polygonal shapes having larger diameters at the lower portion 46 of the shield 42 than at the upper portion 48 of the shield 42, may be used and maintain some of the advantages described herein. In other embodiments, the diameter of the lower portion 46 and the upper portion 48 of the shield 42 may be similar or even the same. However, the diameters of the lower portion 46 and the upper portion 48 of the shield 42 should be larger than the diameter of the outlet member 44.

Moreover, in addition to a bell-shaped design of the shield 42, other shapes or configurations may be used for reducing the spilling, spraying or splashing of fluid onto healthcare workers as long as the diameter of the lower portion 46 of the shield 42 is greater than the diameter of the upper portion 48 of the shield 42. Additionally, in some embodiments, the outlet portion 14 may be designed such that the shield 42 is off-center from the outlet member 44 so that the outlet member 44 is closer to one sidewall 49 than the other. This may allow droplets to form on the side of the outlet member 44 that is farthest from the shield 42, therefore minimizing the chance that urine will collect on the shield 42. Although the angled end portion 45 of the outlet member 44 may be designed to face generally in any direction, i.e., 0-360 degrees, in a preferred orientation, the angled end portion 45 faces toward an area of the shield 42 that is farthest from the angled end portion 45.

The outlet device 10 (not including the valve member 30) may be made of rigid and/or semi-rigid plastic materials and/or combinations of rigid or semi-rigid plastic materials. Examples of rigid and semi-rigid plastic materials that may be used include polyethylene, polypropylene, polycarbonate, polystyrene, and/or combinations thereof. The rigid or semi-rigid plastic materials may be clear or colored plastic. Alternatively, the outlet device 10 may be made of a metal, such as stainless steel. The valve member 30 may be made of a plastic material, such as polypropylene, polyethylene, polycarbonate, ABS (acrylonitrile butadiene styrene), and/or combinations thereof.

It is contemplated that other materials may be used to make the outlet device 10 and valve member 30. For example, materials having certain desirable properties relating to ease of manufacturing, cost, rigidity, etc., may be suitable. Such materials may allow the outlet device 10 to be manufactured as a single, integrated device, which makes manufacture of the outlet device 10 faster and less costly. However, it is also contemplated that the outlet device 10 may be manufactured having one or more parts that are detachable, such as a shield 42 that may be snapped or adhered to the outlet device 10 and may be removable at will. This would allow healthcare workers to remove parts after they have been used and dispose of them. Such parts may also be connectable in order to assemble the outlet device 10.

As shown in FIG. 7, the outlet device 10 is attached at or near the bottom of a drain bag 50 to allow the fluid to flow through the outlet device 10 due to gravitational forces. As discussed above, the connector 22 is inserted into tubing 52 affixed to the drain bag 50. The tubing 52 is often a plastic material, such as vinyl. The valve member 30 in this figure is shown in the closed position such that fluid will not flow out of the outlet device 10. When a healthcare worker needs to withdraw a sample of fluid from or empty the drain bag 50, he or she moves the valve member 30 to the open position to start the flow of fluid through the outlet device 10. Once a sufficient amount of fluid has been withdrawn, the healthcare worker moves the valve member 30 to the closed position to stop the flow of fluid from the outlet device 10.

It should be noted that the outlet device 10 described herein allows a healthcare worker to operate the outlet device 10 with one hand since it is not necessary for a healthcare worker to hold a shield in place to reduce or prevent spilling, splashing or spraying. Furthermore, as the shield 42 of the outlet portion 14 extends a suitable distance below the outlet member 44, there is a reduced chance that accidental contact with the outlet member 44 may occur which could contaminate the outlet device 10 and ultimately infect the patient. In some embodiments, the bell-shaped shield 42 should extend below the outlet member 44 by a length that is at least equal in length to the outlet member 44. This lessens the likelihood of accidental contact of the outlet member 44 by a healthcare worker.

The outlet device 10 described herein may be used with current urinary drain bags on the market. The outlet device described herein addresses the problems of current drain bags that allow fluid to remain on the drain devices and/or tubing. Besides being a general nuisance, there is a concern that contact with the fluid may expose workers to infectious materials. When contact with the fluid occurs, a healthcare worker should then wash his or her hands, face or body thoroughly to remove the fluid. In particular, splashing of fluid may occur when a worker moves the drain device/tubing to or from the drain housing or "keeper" shown in prior art FIGS. 1-3. Furthermore, the outlet device also reduces the chances of contamination of the patient from infectious materials.

The embodiments described herein provide an outlet device 10 that helps to reduce the amount of fluid that remains on the outlet device 10 and, thus, reduces and/or eliminates the spilling, spraying and splashing of fluid on the healthcare worker. This occurs due to the design of the outlet device 10 having an angled outlet member 44 and a bell-shaped shield 42 that has a larger diameter at the lower portion 46 and a smaller diameter at the upper portion 48. Moreover, the present design eliminates the need for a drain housing or "keeper" so that the outlet device 10 is able to hang freely from the drain bag 50. However, the outlet device 10 should not hang too far below the drain bag 50 in order to avoid causing inconvenience to the healthcare worker. In other words, even though the drain bags 50 should be positioned below the patient's bladder in order to work properly, the outlet device 10 is designed to be able to hang from a bed or chair without touching the ground and to give the healthcare worker enough space to drain the bag 50. Furthermore, the healthcare worker does not have to hold the shield 42 in place because the shield 42 is attached and balanced around the outlet member 44 and will not tip to one side or another. Thus, only one hand is needed to operate the outlet device 10. Moreover, the present outlet device 10 eliminates problems due to the possible contamination of a drain housing, as well as reduces the contact with airborne bacteria due to the presence of the shield 42. This reduces the chances of bacteria traveling up the tubing and infecting the patient. Additionally, the outlet device described herein is not limited to use with urinary drain bags, but may be used with other drain bags that collect fluids from patients.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following alternative embodiments.

What is claimed is:

1. An outlet device for connecting to a fluid drain bag and adapted to eliminate the use of a drain housing, the outlet device comprising:
    an inlet portion including a connector and a cylindrical portion, a first end of the connector adapted to connect to the fluid drain bag and a second end of the connector adapted to connect to a first end of the cylindrical portion thereby forming a generally longitudinal opening therethrough;
    a valve portion connected to a second end of the cylindrical portion and further forming the longitudinal opening, the valve portion containing a valve member for moving between a first position for permitting fluid flow through the longitudinal opening and a second position for obstructing fluid flow through the longitudinal opening; and
    an outlet portion connected to the valve portion, the outlet portion including a shield and an outlet member surrounded by the shield, the shield extending a distance below the outlet member and having an upper portion and a lower portion wherein the diameter of the upper portion is less than the diameter of the lower portion,
    wherein the outlet member is in fluid communication with the longitudinal opening of the valve portion and the inlet portion and includes an angled end portion for reducing the amount of fluid that may collect on the perimeter of the outlet member,
    and wherein the shield is not centered around the outlet member and the angled end portion faces toward an area of the shield that is farthest from the angled end portion.

2. The drain bag outlet device of claim 1, wherein the outlet member and shield assist in reducing contact of fluid onto a healthcare worker.

3. The drain bag outlet device of claim 1, wherein the valve member is a slide valve for slidably moving between the first position and the second position.

4. The drain bag outlet device of claim 1, wherein the shield is bell-shaped.

5. The drain bag outlet device of claim 1, wherein the shield is oval-shaped.

6. The drain bag outlet device of claim 1, wherein the shield is circular-shaped.

7. The drain bag outlet device of claim 1, wherein the inlet portion, the valve portion and the outlet portion are integrally formed to form a single device that is connected to the fluid drain bag.

8. The drain bag outlet device of claim 1, wherein one or more of the inlet portion, the valve portion and the outlet portion are separate components that are attached to form a single unit.

9. The drain bag outlet device of claim 1, wherein the connector includes a flange that is inserted into tubing associated with the fluid drain bag.

10. The drain bag outlet device of claim 1, wherein the shield extends a sufficient distance below the outlet member to reduce contact with the outlet member.

11. The drain bag outlet device of claim 1, wherein the shield is detachably coupled to the outlet device.

12. The drain bag outlet device of claim 1, wherein the shield is removably coupled to the valve portion via adhesion bonding or solvent bonding.

13. The drain bag outlet device of claim 1, wherein the drain bag outlet device can be operated with a single hand.

14. The drain bag outlet device of claim 1, wherein the fluid is urine.

15. The drain bag outlet device of claim 1, wherein the drain bag outlet device is made from polyethylene, propylene, polycarbonate, polystyrene, or combinations thereof.

16. The drain bag outlet device of claim 1, wherein the drain bag outlet device is made from stainless steel.

17. A container system for collecting and discharging fluid, the container system comprising:
    a chamber for holding fluid;
    an outlet device connected to the chamber, the outlet device comprising an inlet portion, a valve portion and an outlet portion, wherein the inlet portion includes a connector and a cylindrical portion, a first end of the connector adapted to connect to the chamber and a second end of the connector adapted to connect to a first end of the cylindrical portion thereby forming a generally longitudinal opening therethrough which is in fluid communication with the chamber, the valve portion connected to a second end of the cylindrical portion and containing a valve member for moving between a first position for permitting fluid flow through the longitudinal opening and a second position for obstructing fluid flow through the longitudinal opening, the outlet portion attached to the valve portion and including a shield and an outlet member in fluid communication with the longitudinal opening, wherein the shield completely surrounds the outlet member and extends below the outlet member, the shield having an upper portion and a lower portion wherein the diameter of the upper portion is less than the diameter of the lower portion, the outlet member having an angled end portion for directing fluid as it flows through the longitudinal opening, wherein the shield is not centered around the outlet member and the angled end portion faces toward an area of the shield that is farthest from the angled end portion, and wherein the outlet device is in fluid communication with the chamber such that a portion of the fluid can be removed from the chamber by moving the valve member from the first position to the second position and allowing fluid to flow through the outlet device.

18. The container system of claim 17, wherein the shield is bell-shaped.

19. The container system of claim 17, wherein the shield is oval-shaped.

20. The container system of claim 17, wherein the shield is circular-shaped.

21. The container system of claim 17, wherein the fluid is urine.

22. The container system of claim 17, wherein the outlet member and shield assist in reducing contact of fluid onto a healthcare worker.

23. The container system of claim 17, wherein the valve member is a slide valve for slidably moving between the first position and the second position.

24. The container system of claim 17, wherein the inlet portion, the valve portion and the outlet portion are integrally formed to form a single device that is connected to chamber.

25. The container system of claim 17, wherein one or more of the inlet portion, the valve portion and the outlet portion are separate components that are attached to form a single unit.

26. The container system of claim 17, wherein the connector includes a flange that is inserted into tubing associated with the chamber.

27. The container system of claim 17, wherein the shield extends a sufficient distance below the outlet member to reduce contact with the outlet member.

28. The container system of claim 17, wherein the shield is detachable from the outlet device after use.

29. The container system of claim 17, wherein upon removal, the shield is disposable and a second shield is connectable to the outlet device.

30. The container system of claim 17, wherein the outlet device can be operated with a single hand.

31. The container system of claim 17, wherein the outlet device is made from polyethylene, propylene, polycarbonate, polystyrene, or combinations thereof.

32. The container system of claim 17, wherein the outlet device is made from stainless steel.

* * * * *